United States Patent
Hariprasad et al.

(10) Patent No.: US 11,072,586 B2
(45) Date of Patent: Jul. 27, 2021

(54) SOLID STATE FORMS OF ELTROMBOPAG CHOLINE

(71) Applicant: ASSIA CHEMICAL INDUSTRIES LTD., Petach Tikva (IL)

(72) Inventors: Sharma Vijay Hariprasad, Thane (IN); Nasir Ali Shafakat Ali, Thane (IN); Joshi Ashutosh Vijay, Thane (IN); Parven Kumar Luthra, Thane (IN); Anantha Rajmohan Muthusamy, Sivakasi (IN); Amit Singh, Greater Noida (IN); Rajesh Sadanand Bate, Thane (IN); Sadanand Hardeo Maurya, Thane (IN)

(73) Assignee: ASSIA CHEMICAL INDUSTRIES LTD., Petach Tikva (IL)

( * ) Notice: Subject to any disclaimer, the term of this patent is extended or adjusted under 35 U.S.C. 154(b) by 0 days.

(21) Appl. No.: 16/753,363

(22) PCT Filed: Oct. 5, 2018

(86) PCT No.: PCT/US2018/054582
§ 371 (c)(1),
(2) Date: Apr. 3, 2020

(87) PCT Pub. No.: WO2019/071111
PCT Pub. Date: Apr. 11, 2019

(65) Prior Publication Data
US 2020/0331862 A1  Oct. 22, 2020

(30) Foreign Application Priority Data

Oct. 6, 2017 (IN) .............................. 201711035444
Aug. 24, 2018 (IN) .............................. 201811031840

(51) Int. Cl.
*C07D 231/46* (2006.01)

(52) U.S. Cl.
CPC ........ *C07D 231/46* (2013.01); *C07B 2200/13* (2013.01)

(58) Field of Classification Search
CPC ..................................................... C07D 231/46
See application file for complete search history.

(56) References Cited

FOREIGN PATENT DOCUMENTS

WO  2017042839 A1  3/2017

OTHER PUBLICATIONS

Salts and Polymorphs of (Z)-3'-(2-(1-(3,4-Dimethylphenyl)-3-Methyl-5-Oxo-1H-Pyrazol-4(5H)-Ylidene)Hydr Azinyl)-2'-Hydroxybiphenyl-3-Carboxylic Acid ip.com Journal, ip.com I NC., West Henrietta, NY, us, Mar. 2, 2011 ( XP013144170).
International Search Report and Written Opinion of the International Searching Authority issued in corresponding Appl. No. PCT/US2018/054582 dated Dec. 6, 2018 (13 pages).

*Primary Examiner* — Kamal A Saeed
(74) *Attorney, Agent, or Firm* — Carter, DeLuca & Farrell LLP

(57) ABSTRACT

Solid state forms of Eltrombopag choline, processes for preparation thereof and pharmaceutical compositions thereof are disclosed.

13 Claims, 10 Drawing Sheets

Figure 1: An X-ray powder diffractogram (XRPD) of form A of Eltrombopag choline
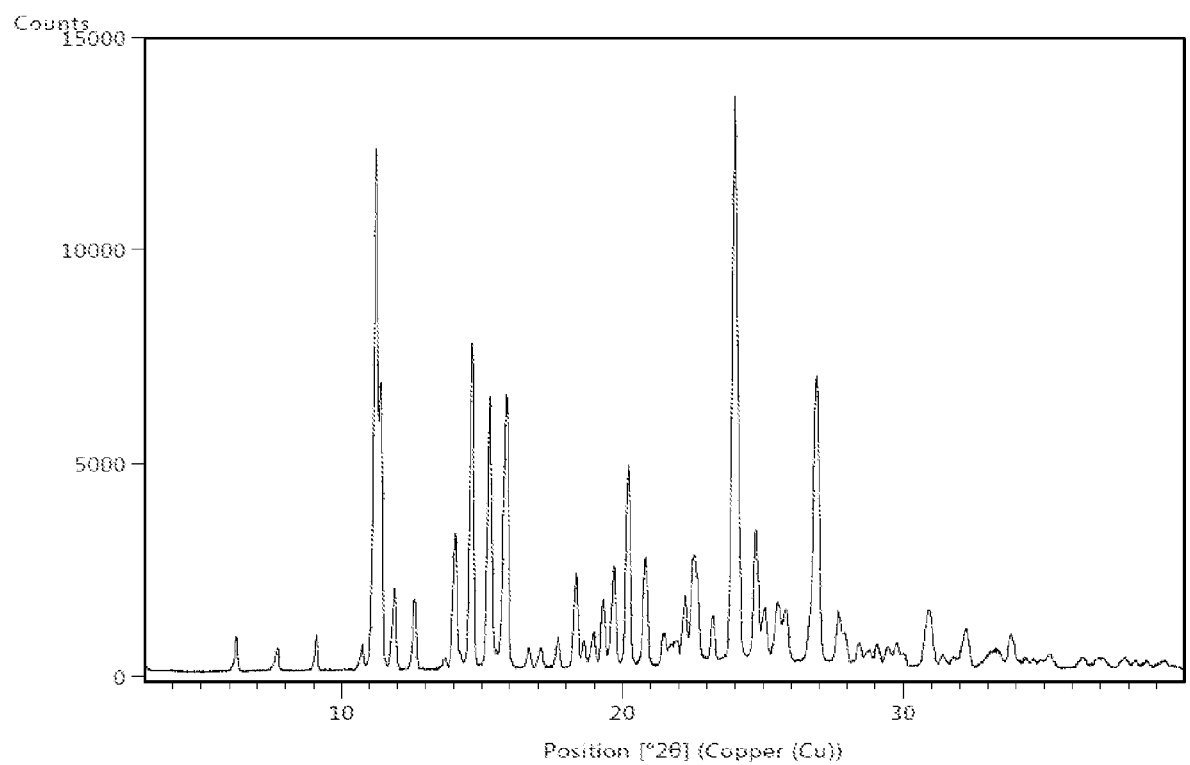

Figure 2: An X-ray powder diffractogram (XRPD) of form B of Eltrombopag choline.
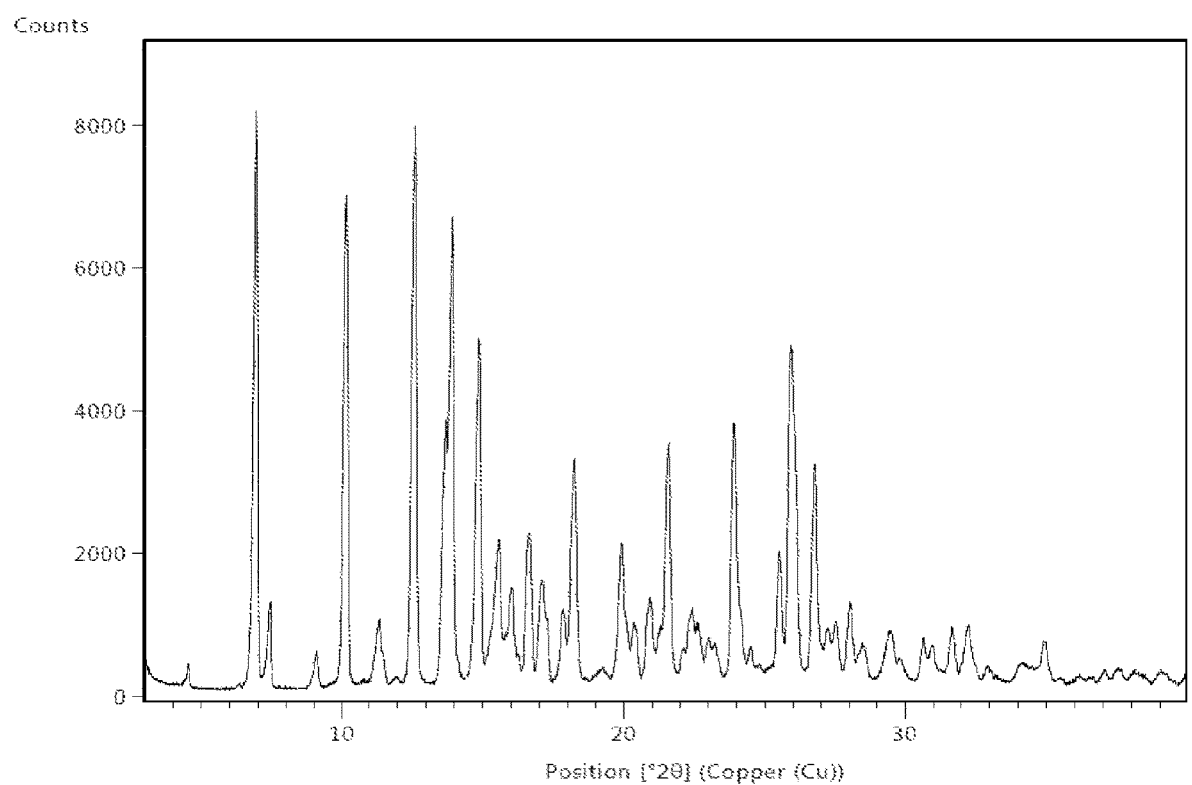

Figure 3: solid state $^{13}$C-NMR spectrum of form A of Eltrombopag choline.
(Figure 3A, -40-240 ppm; Figure 3B, 0-100ppm; Figure 3C 100-240ppm)
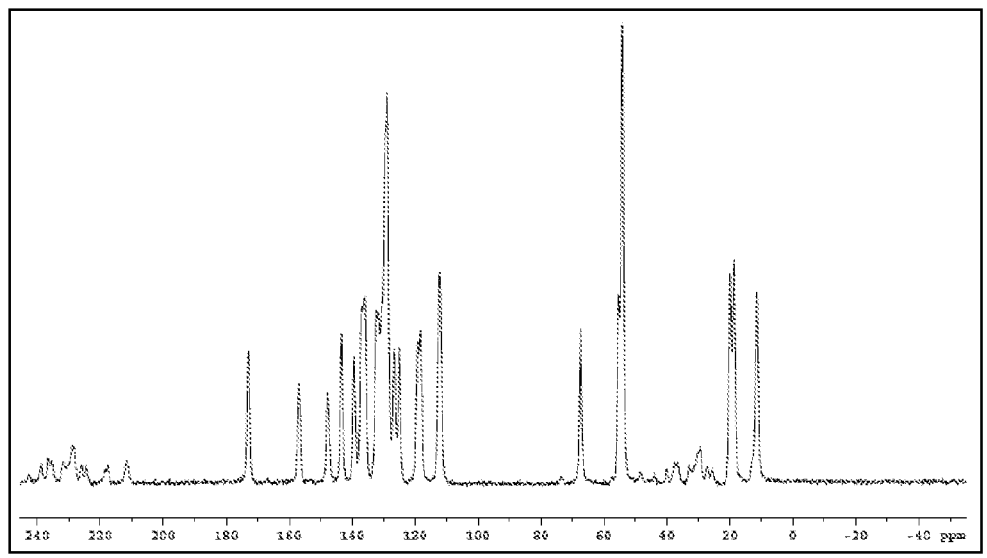
Figure 3A: solid state $^{13}$C-NMR spectrum of form A of Eltrombopag choline.
(-40-240 ppm)

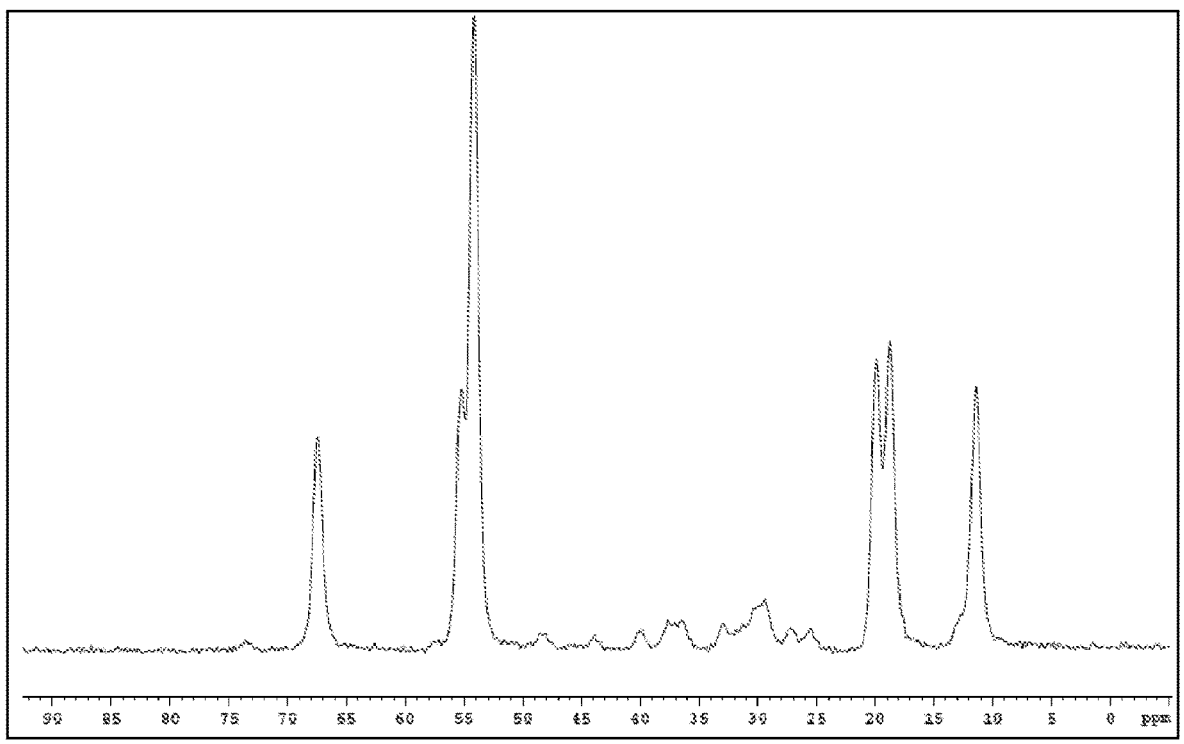
Figure. 3B: solid state $^{13}$C-NMR spectrum of form A of Eltrombopag choline. (0-100ppm)

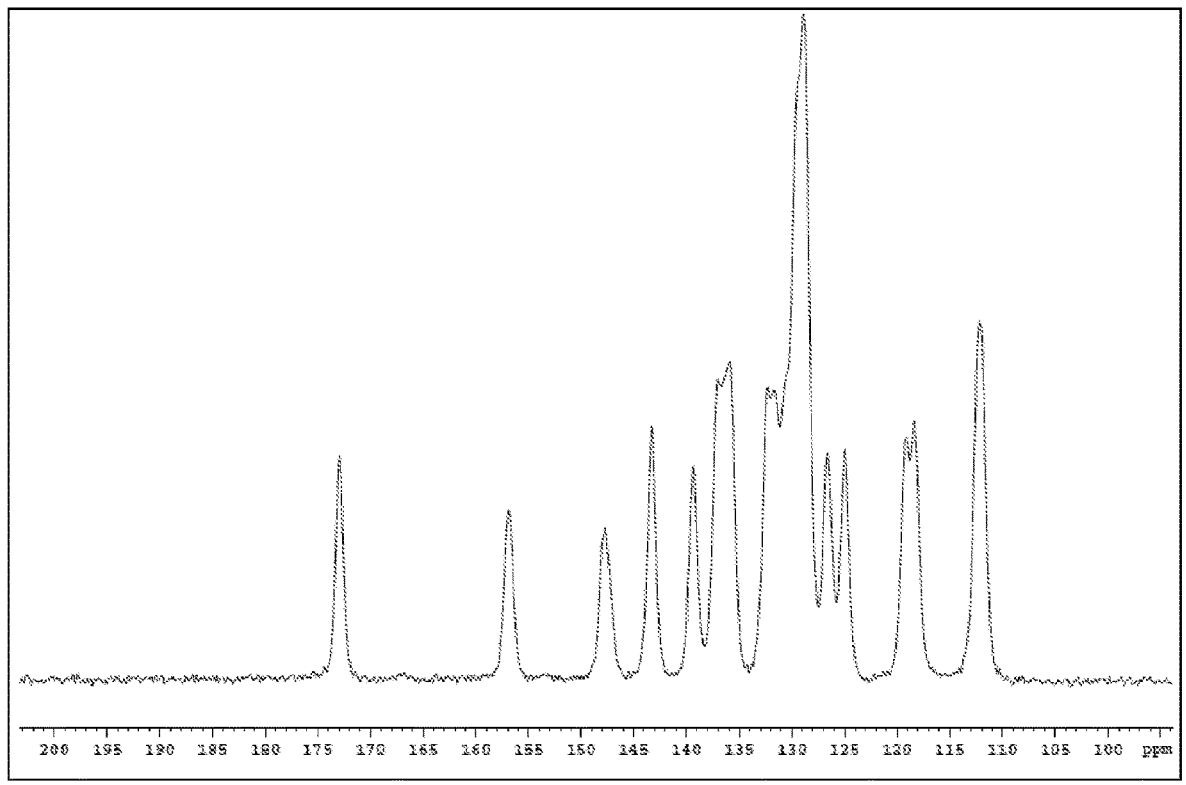
Figure 3C: solid state $^{13}$C-NMR spectrum of form A of Eltrombopag choline. (100-240ppm)

Figure 4: solid state $^{13}$C-NMR spectrum of form B of Eltrombopag choline.
(Figure 4A, -40-240 ppm; Figure 4B, 0-100ppm; Figure 4C 100-240ppm)
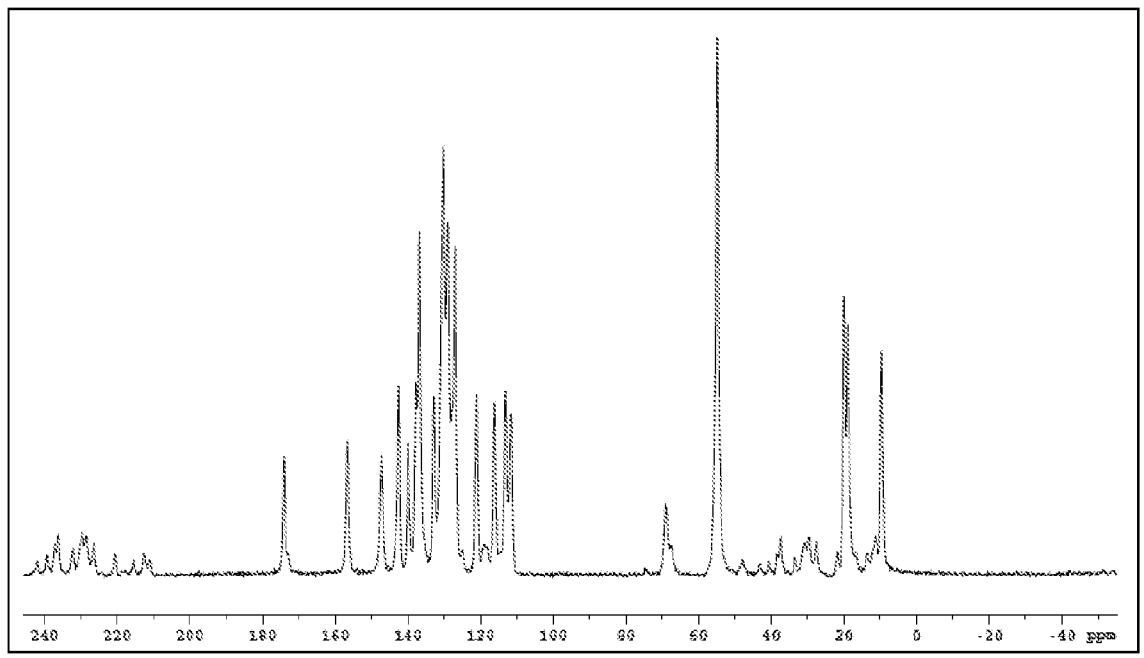
Figure 4A: solid state $^{13}$C-NMR spectrum of form B of Eltrombopag choline.
(-40-240 ppm)

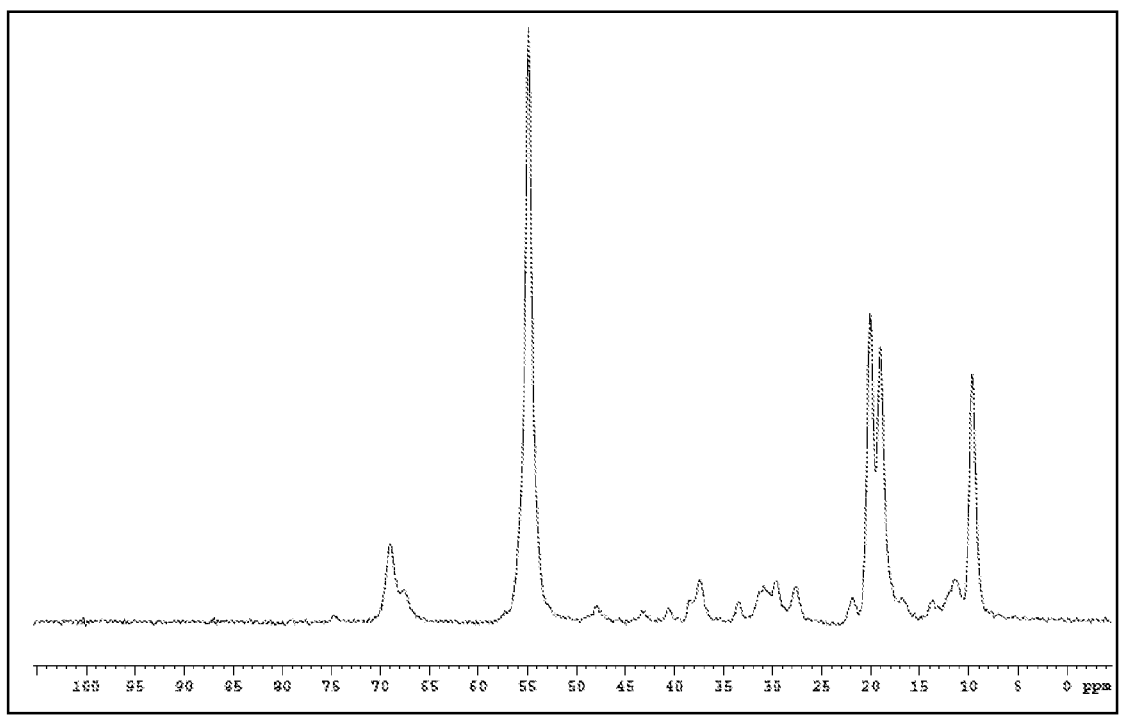
Figure 4B: solid state $^{13}$C-NMR spectrum of form B of Eltrombopag choline. (0-100ppm)

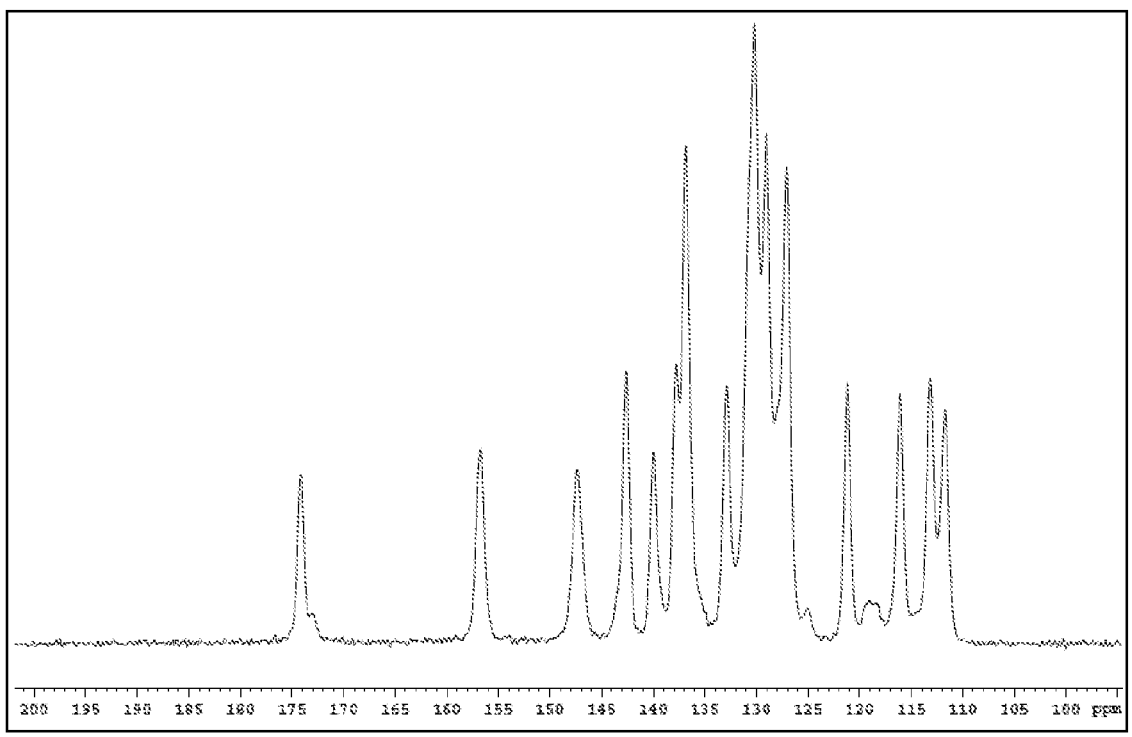
Figure 4C: solid state $^{13}$C-NMR spectrum of form B of Eltrombopag choline. (100-240ppm)

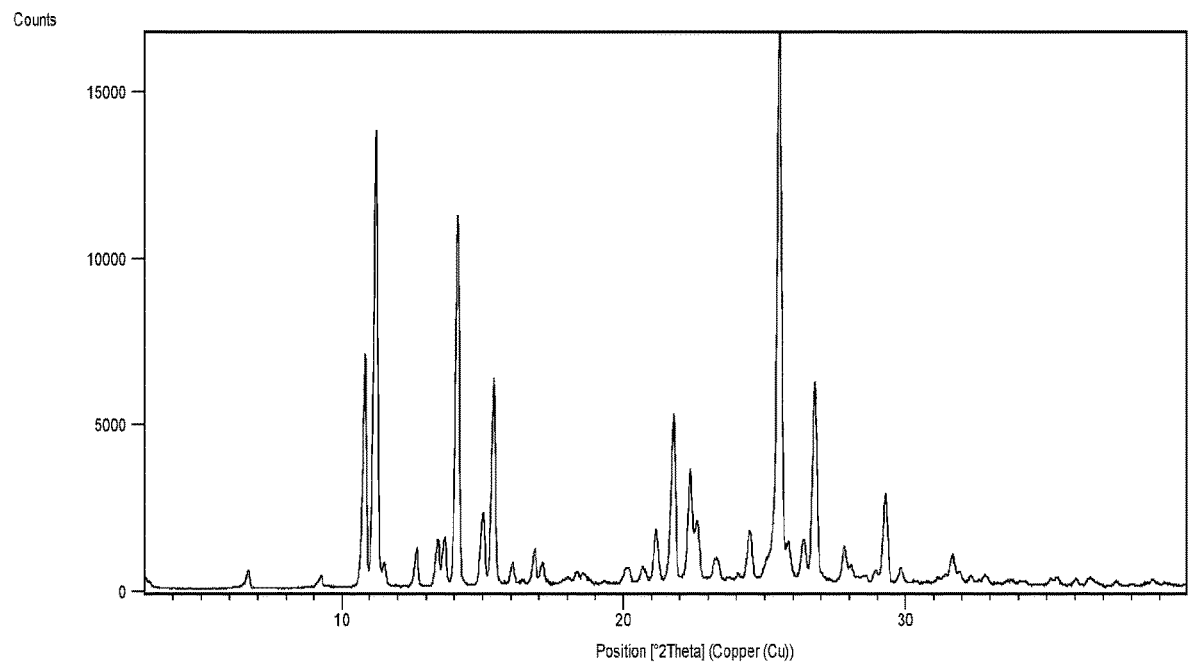
Figure 5: An X-ray powder diffractogram (XRPD) of form C of Eltrombopag choline.

Figure 6: An X-ray powder diffractogram (XRPD) of amorphous form of Eltrombopag choline
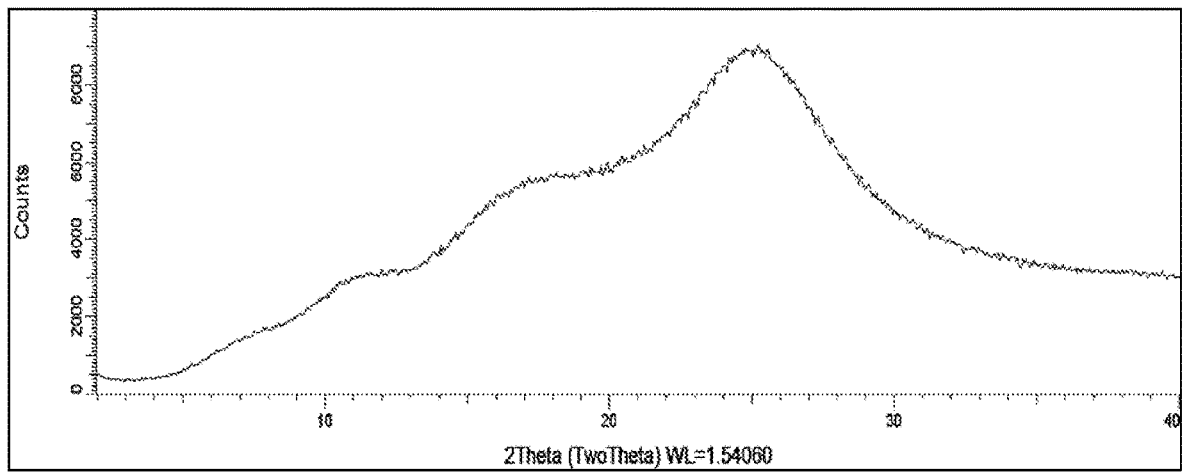

SOLID STATE FORMS OF ELTROMBOPAG CHOLINE

CROSS REFERENCE TO RELATED APPLICATIONS

This application is a National Stage of, and claims priority to and the benefit of, International Patent Application No. PCT/US2018/054582 filed on Oct. 5, 2018, which, in turn, claims the benefit of, and priority to, IN Provisional Patent Application No. 201711035444, filed Oct. 6, 2017 and IN Provisional Patent Application 201811031840, filed on Aug. 24, 2018, the entire disclosures of each of which are incorporated by reference herein.

FIELD OF THE INVENTION

The present disclosure relates to solid state forms of Eltrombopag choline, processes for preparation thereof and pharmaceutical compositions thereof.

BACKGROUND OF THE INVENTION

Eltrombopag has the chemical name 3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid.

Eltrombopag has the following chemical structure:

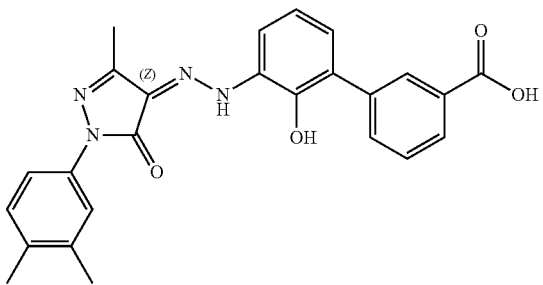 [SMILES: CC1=NN(c2ccc(C)c(C)c2)C(=O)/C1=N\Nc1cccc(-c2cccc(C(=O)O)c2)c1O]

Eltrombopag is a small-molecule, non-peptide thrombopoitin (TPO) receptor agonist that has been shown in pre-clinical research and clinical trials to stimulate the proliferation and differentiation of megakaryocytes, the bone marrow cells that give rise to blood platelets.

Eltrombopag bisethanolamine is the active ingredient of the marketed drug PROMACTA® (US) or REVOLADE® (EU) for the treatment of Idiopathic thrombocytopenic purpura, Thrombocytopenia and Aplastic anemia.

Eltrombopag is disclosed in U.S. Pat. No. 7,160,870. Eltrombopag bisethanolamine salt is disclosed in U.S. Pat. No. 7,547,719. Eltrombopag tromethamine salt is disclosed in WO20170042839.

Polymorphism, the occurrence of different crystal forms, is a property of some molecules and molecular complexes. A single compound, like Eltrombopag choline, may give rise to a variety of polymorphs having distinct crystal structures and physical properties like melting point, thermal behaviors (e.g. measured by thermogravimetric analysis—"TGA", or differential scanning calorimetry—"DSC"), X-ray powder diffraction (XRPD) pattern, infrared absorption fingerprint, Raman absorption fingerprint, and solid state ($^{13}C$-) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, improving the dissolution profile, or improving stability (polymorph as well as chemical stability) and shelf-life. These variations in the properties of different salts and solid state forms may also provide improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to use variations in the properties and characteristics of a solid active pharmaceutical ingredient for providing an improved product.

Discovering new salts, solid state forms and solvates of a pharmaceutical product can provide materials having desirable processing properties, such as ease of handling, ease of processing, storage stability, and ease of purification or as desirable intermediate crystal forms that facilitate conversion to other salts or polymorphic forms. New salts, polymorphic forms and solvates of a pharmaceutically useful compound can also provide an opportunity to improve the performance characteristics of a pharmaceutical product (dissolution profile, bioavailability, etc.). It enlarges the repertoire of materials that a formulation scientist has available for formulation optimization, for example by providing a product with different properties, e.g., a different crystal habit, higher crystallinity or polymorphic stability which may offer better processing or handling characteristics, improved dissolution profile, or improved shelf-life.

For at least these reasons, there is a need for additional solid state forms (including solvated forms) of Eltrombopag choline.

SUMMARY OF THE INVENTION

The present disclosure relates to solid state forms of Eltrombopag choline, processes for preparation thereof, and pharmaceutical compositions comprising these solid state forms.

The present disclosure also provides uses of the solid state forms of Eltrombopag choline for preparing other solid state forms of Eltrombopag, Eltrombopag salts and solid state forms thereof.

The present disclosure also provides solid state forms of Eltrombopag choline of the present disclosure for uses in the preparation of other solid state forms of Eltrombopag, Eltrombopag salts and solid state forms thereof.

The present disclosure further provides processes for preparing other solid state forms of Eltrombopag, Eltrombopag salts and solid state forms thereof.

In another embodiment, the present disclosure encompasses the described solid state forms of Eltrombopag choline for uses in the preparation of pharmaceutical compositions and/or formulations, optionally for the treatment of Idiopathic thrombocytopenic purpura, Thrombocytopenia and Aplastic anemia.

In another embodiment, the present disclosure encompasses uses of the described solid state form of Eltrombopag choline for the preparation of pharmaceutical compositions and/or formulations.

The present disclosure further provides pharmaceutical compositions comprising the solid state form of Eltrombopag choline according to the present disclosure.

In yet another embodiment, the present disclosure encompasses pharmaceutical formulations comprising the described solid state forms of Eltrombopag choline and at least one pharmaceutically acceptable excipient.

The present disclosure encompasses processes to prepare said pharmaceutical formulations of Eltrombopag choline comprising combining the described solid state form and at least one pharmaceutically acceptable excipient.

The solid state forms defined herein as well as the pharmaceutical compositions or formulations of the solid state form of Eltrombopag choline can be used as medicaments, particularly for the treatment of Idiopathic thrombocytopenic purpura, Thrombocytopenia and Aplastic anemia The present disclosure also provides methods of treating of Idiopathic thrombocytopenic purpura, Thrombocytopenia and Aplastic anemia; comprising administering a therapeutically effective amount of the solid state form of Eltrombopag choline of the present disclosure, or at least one of the herein described pharmaceutical compositions or formulations, to a subject suffering from Idiopathic thrombocytopenic purpura, Thrombocytopenia and Aplastic anemia, or otherwise in need of the treatment.

The present disclosure also provides uses of the solid state forms of Eltrombopag choline of the present disclosure, or at least one of the above pharmaceutical compositions or formulations for the manufacture of medicaments for treating Idiopathic thrombocytopenic purpura, Thrombocytopenia and Aplastic anemia.

According to the Food and Nutritions Board of the National Institute of Medicine the adequate intake for choline is 200-600 mg daily for adults and for children between 125-375 mg/day depending on age. For Eltrombopag choline, equivalent intake of the counterion of 588.3 mg/day is well tolerable.

BRIEF DESCRIPTION OF THE FIGURES

FIG. 1 shows an X-ray powder diffractogram (XRPD) of form A of Eltrombopag choline.

FIG. 2 shows an X-ray powder diffractogram (XRPD) of form B of Eltrombopag choline.

FIG. 3 shows a solid state $^{13}$C-NMR spectrum of form A of Eltrombopag choline. (FIG. 3A, −40-240 ppm; FIG. 3B, 0-100 ppm; FIG. 3C 100-200 ppm)

FIG. 4 shows a solid state $^{13}$C-NMR spectrum of form B of Eltrombopag choline (FIG. 4A, −40-240 ppm; FIG. 4B, 0-100 ppm; FIG. 4C 100-200 ppm).

FIG. 5 shows an X-ray powder diffractogram (XRPD) of form C of Eltrombopag choline FIG. 6 shows a shows an X-ray powder diffractogram (XRPD) of amorphous Eltrombopag choline

DETAILED DESCRIPTION OF THE INVENTION

The present disclosure relates to a solid state form of Eltrombopag choline, processes for preparation thereof and pharmaceutical compositions comprising this solid state form. The disclosure also relates to the conversion of the described solid state form of Eltrombopag choline to other solid state forms of Eltrombopag, Eltrombopag salts and their solid state forms.

The solid state form of Eltrombopag choline according to the present disclosure may have advantageous properties selected from at least one of: chemical or polymorphic purity, flowability, solubility, dissolution rate, bioavailability, morphology or crystal habit, stability—such as chemical stability as well as thermal and mechanical stability with respect to polymorphic conversion, stability towards dehydration and/or storage stability, a lower degree of hygroscopicity, low content of residual solvents and advantageous processing and handling characteristics such as compressibility, or bulk density.

A crystal form may be referred to herein as being characterized by graphical data "as depicted in" a Figure. Such data include, for example, powder X-ray diffractograms and solid state NMR spectra. As is well-known in the art, the graphical data potentially provides additional technical information to further define the respective solid state form (a so-called "fingerprint") which can not necessarily be described by reference to numerical values or peak positions alone. In any event, the skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of Eltrombopag choline referred to herein as being characterized by graphical data "as depicted in" a Figure will thus be understood to include any crystal forms of the Eltrombopag choline, characterized with the graphical data having such small variations, as are well known to the skilled person, in comparison with the Figure.

A solid state form (or polymorph) may be referred to herein as polymorphically pure or as substantially free of any other solid state (or polymorphic) forms. As used herein in this context, the expression "substantially free of any other forms" will be understood to mean that the solid state form contains about 20% or less, about 10% or less, about 5% or less, about 2% or less, about 1% or less, or 0% of any other forms of the subject compound as measured, for example, by XRPD. Thus, the solid state form of Eltrombopag choline described herein as substantially free of any other solid state forms would be understood to contain greater than about 80% (w/w), greater than about 90% (w/w), greater than about 95% (w/w), greater than about 98% (w/w), greater than about 99% (w/w), or a100% of the subject solid state form of Eltrombopag choline. Accordingly, in some embodiments of the disclosure, the described solid state forms of Eltrombopag choline may contain from about 1% to about 20% (w/w), from about 5% to about 20% (w/w), or from about 5% to about 10% (w/w) of one or more other solid state forms of the same Eltrombopag choline.

As used herein, unless stated otherwise, XRPD peaks reported herein are optionally measured using CuK$_\alpha$ radiation, λ=1.5418 Å.

As used herein, the term "isolated" in reference to solid state forms of Eltrombopag choline of the present disclosure corresponds to solid state form of Eltrombopag choline that is physically separated from the reaction mixture in which it is formed.

A thing, e.g., a reaction mixture, may be characterized herein as being at, or allowed to come to "room temperature", often abbreviated "RT." This means that the temperature of the thing is close to, or the same as, that of the space, e.g., the room or fume hood, in which the thing is located. Typically, room temperature is from about 20° C. to about 30° C., about 22° C. to about 27° C., or about 25° C.

A processor step may be referred to herein as being carried out "overnight." This refers to a time interval, e.g., for the process or step, that spans the time during the night, when that process or step may not be actively observed. This time interval is from about 8 to about 20 hours, about 10 to about 18 hours, or about 16 hours.

As used herein, the expression "wet crystalline form" refers to a polymorph that was not dried using any conventional techniques to remove residual solvent. Examples for such conventional techniques can be, but not limited to, evaporation, vacuum drying, oven drying, drying under nitrogen flow, etc.

As used herein, the expression "dry crystalline form" refers to a polymorph that was dried using any conventional techniques to remove residual solvent. Examples of such conventional techniques can be, but are not limited to, evaporation, vacuum drying, oven drying, drying under nitrogen flow, etc.

As used herein, and unless stated otherwise, the term "anhydrous" in relation to crystalline Eltrombopag choline relates to crystalline Eltrombopag choline which does not include any crystalline water (or other solvents) in a defined, stoichiometric amount within the crystal. Moreover, an "anhydrous" form does not contain more than about 1% (w/w) of either water or organic solvents as measured for example by TGA.

The term "solvate", as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

As used herein, the term "reduced pressure" refers to a pressure of about 10 mbar to about 500 mbar.

The present disclosure comprises a crystalline form of Eltrombopag choline designated as Form A. The crystalline Form A of Eltrombopag choline can be characterized by data selected from one or more of the following: an XRPD pattern having peaks at 11.3, 14.7, 15.4, 16.0 and 24.1 degrees-2-theta±0.2 degrees-2-theta; an XRPD pattern as depicted in FIG. 1; and combinations of these data. Crystalline Form A of Eltrombopag choline may be further characterized by the XRPD pattern having peaks at 11.3, 14.7, 15.4, 16.0 and 24.1 degrees 2-theta±0.2 degrees 2-theta, and also having one, two, three, four, five, six or seven additional peaks selected from 12.0, 12.7, 14.1, 20.3, 20.9, 24.8 and 27.0 degrees 2-theta±0.2 degrees 2-theta.

Crystalline Form A of Eltrombopag choline may be characterized by each of the above characteristics alone/or by all possible combinations, e.g. by XRPD pattern having peaks at 11.3, 14.7, 15.4, 16.0 and 24.1 degrees 2-theta±0.2 degrees 2-theta and an XRPD pattern as depicted in FIG. 1.

Crystalline Form A of Eltrombopag choline may alternatively or additionally be characterized by data selected from one or more of the following: a solid state $^{13}$C-NMR spectrum with peaks at 112.2, 125.0, 126.6, 128.9, 143.3 and 172.9 ppm±0.2 ppm; or by a solid state $^{13}$C-NMR spectrum having the following chemical shift absolute differences from a peak at 156.9 ppm±2 ppm of 44.8, 31.9, 30.3, 28.0, 13.6 and 16.0 ppm±0.1 ppm; or a solid state $^{13}$C NMR spectrum having chemical shift difference from a peak at 112.2 ppm±1 ppm of 44.8 ppm±0.1 ppm; or by a solid state $^{13}$C-NMR spectrum substantially as depicted in FIG. 3; or combinations of these data.

In an embodiment, crystalline Form A of Eltrombopag choline is anhydrous.

The present disclosure further comprises a crystalline form of Eltrombopag choline designated as Form B. The crystalline Form B of Eltrombopag choline can be characterized by data selected from one or more of the following: an XRPD pattern having peaks at 7.0, 10.2, 13.9, 14.9, 18.3, 21.6 and 26.0 degrees 2-theta±0.2 degrees 2-theta; an XRPD pattern as depicted in FIG. 2; and combinations of these data. Crystalline Form B of Eltrombopag choline may be further characterized by the XRPD pattern having peaks at 7.0, 10.2, 13.9, 14.9, 18.3, 21.6 and 26.0 degrees 2-theta±0.2 degrees 2-theta, and also having one, two, three, or four additional peaks selected from 7.4, 16.7, 19.9 and 23.9 degrees 2-theta±0.2 degrees 2-theta.

Crystalline Form B of Eltrombopag choline may be characterized by each of the above characteristics alone/or by all possible combinations, e.g. by XRPD pattern having peaks at 7.0, 10.2, 13.9, 14.9, 18.3, 21.6 and 26.0 degrees 2-theta±0.2 degrees 2-theta and an XRPD pattern as depicted in FIG. 2.

Crystalline Form B of Eltrombopag choline may alternatively or additionally be characterized by data selected from one or more of the following: a solid state $^{13}$C-NMR spectrum with peaks at 121.2, 127.1, 129.1, 130.2, 142.6 and 174.1 ppm±0.2 ppm; or by a solid state $^{13}$C-NMR spectrum having the following chemical shift absolute differences from a peak at 156.74 ppm 2 ppm of 35.5, 29.7, 27.7, 26.5, 14.1 and 17.4 ppm±0.1 ppm; or a solid state $^{13}$C NMR spectrum having chemical shift difference from a peak at 121.2 ppm±1 ppm of 35.5 ppm±0.1 ppm; or by a solid state $^{13}$C-NMR spectrum substantially as depicted in FIG. 4; or combinations of these data.

Crystalline Form B of Eltrombopag choline (1:1) may be a hydrate. In certain embodiments form B may contain from about 3% to about 9% of water by weight as measured by Karl Fischer titrator and TGA. In certain embodiments, crystalline Form B of Eltrombopag choline may be a trihydrate.

The present disclosure further comprises a crystalline form of Eltrombopag choline designated as Form C. The crystalline Form C of Eltrombopag choline can be characterized by data selected from one or more of the following: an XRPD pattern having peaks at 10.9, 14.2, 15.5, 21.9 and 26.9 degrees 2-theta±0.2 degrees 2-theta; an XRPD pattern as depicted in FIG. 5; and combinations of these data. Crystalline Form C of Eltrombopag choline may be further characterized by the XRPD pattern having peaks at 10.9, 14.2, 15.5, 21.9 and 26.9 degrees 2-theta±0.2 degrees 2-theta, and also having one, two, three, or four additional peaks selected from 11.3, 15.0, 21.2, 22.5 and 25.6 degrees 2-theta±0.2 degrees 2-theta. Form C may be a 2-Methoxyethanol solvate.

The present disclosure further comprises amorphous form of Eltrombopag choline as shown in FIG. 6. Amorphous form of Eltrombopag Choline Salt has the glass transition (Tg) of about 111.95° C.

The present disclosure also provides the use of the solid state form of Eltrombopag choline for preparing other solid state forms of Eltrombopag, Eltrombopag salts and their solid state forms thereof.

The present disclosure also provides the solid state form of Eltrombopag choline of the present disclosure for use in the preparation of other solid state forms of Eltrombopag, Eltrombopag salts and solid state forms thereof.

The present disclosure further encompasses processes for preparing Eltrombopag choline or solid state forms thereof. The process comprises preparing Eltrombopag free acid, and converting it to Eltrombopag choline salt. The conversion can be done, for example, by processes comprising reacting Eltrombopag free acid with choline to obtain the corresponding base-addition salt.

In another embodiment, the present disclosure encompasses the above described solid state forms of Eltrombopag choline for use in the preparation of pharmaceutical compositions and/or formulations, optionally for the treatment of Idiopathic thrombocytopenic purpura, Thrombocytopenia and Aplastic anemia.

In another embodiment, the present disclosure encompasses the use of the above described solid state forms of Eltrombopag choline for the preparation of pharmaceutical compositions and/or formulations. The present disclosure also provides the solid state forms of Eltrombopag choline of the present disclosure for use in the preparation of pharmaceutical compositions and/or formulations.

The present disclosure further provides pharmaceutical compositions comprising the solid state form of Eltrombopag choline according to the present disclosure.

In yet another embodiment, the present disclosure encompasses pharmaceutical formulations comprising the above described solid state form of Eltrombopag choline and at least one pharmaceutically acceptable excipient.

The present disclosure encompasses processes to prepare said formulations of Eltrombopag choline comprising combining the above solid state form of Eltrombopag choline and at least one pharmaceutically acceptable excipient.

The solid state forms of Eltrombopag choline as defined herein, as well as the pharmaceutical compositions or formulations thereof and at least can be used as medicaments, particularly for the treatment of Idiopathic thrombocytopenic purpura, Thrombocytopenia and Aplastic anemia.

The present disclosure also provides methods of treating Idiopathic thrombocytopenic purpura, Thrombocytopenia and Aplastic anemia; comprising administering a therapeutically effective amount of the solid state forms of Eltrombopag choline in the present disclosure, or at least one of the above pharmaceutical compositions or formulations, to a subject suffering from Idiopathic thrombocytopenic purpura, Thrombocytopenia and Aplastic anemia, or otherwise in need of the treatment.

The present disclosure also provides use of the solid state form of Eltrombopag choline the present disclosure, or at least one of the above pharmaceutical compositions or formulations for the manufacture of a medicament for treating Idiopathic thrombocytopenic purpura, Thrombocytopenia and Aplastic anemia.

Having described the disclosure with reference to certain preferred embodiments, other embodiments will become apparent to one skilled in the art from consideration of the specification. The disclosure is further illustrated by reference to the following examples describing in detail the preparation of the composition and methods of use of the disclosure. It will be apparent to those skilled in the art that many modifications, both to materials and methods, may be practiced without departing from the scope of the disclosure.

Analytical Methods
X-Ray Powder Diffraction Method:
X-ray diffraction was performed on X-Ray powder diffractometer:
X'Pert PRO PANalytical; CuKα radiation (λ=1.5418 Å); PIXcel detector; laboratory temperature 22-25° C.; The samples were gently ground by means of mortar and pestle in order to obtain a fine powder.
Measurement parameters:
Scan range (°): 3.000-40.001
Step size (°): 0.0131

X-Ray Powder Diffraction Method for Examples 7 and 8:
X-ray diffraction was performed on X-Ray powder diffractometer:
Bruker D8 Advance; CuK_radiation (λ=1.5418 Å); Lynx eye detector; laboratory temperature 22-25° C.; PMMA specimen holder ring. Prior to analysis, the samples were gently ground by means of mortar and pestle in order to obtain a fine powder. The ground sample was adjusted into a cavity of the sample holder and the surface of the sample was smoothed by means of a cover glass.
Measurement Parameters:
Scan range: 2-40 degrees 2-theta;
Scan mode: continuous;
Step size: 0.05 degrees; The described peak positions were determined using silicon powder as an internal standard in an admixture with the sample measured. The position of the silicon (Si) peak was corrected to silicone theoretical peak: 28.45 degrees 2-theta, and the positions of the measured peaks were corrected respectively (presented figures do not describe the Si peak).

Solid-State $^{13}$C NMR Method

Solid-state $^{13}$C NMR spectra were recorded with variable amplitude cross polarization, magic angle spinning and high power proton decoupling using a BRUKER Avance III+ spectrometer operating at 400 MHZ at room temperature. A probe using 4 mm o.d. zirconia rotors was employed. The operation conditions were: contact time: 3 ms; recycle delay: 2 s; 5100 scans and spin rate of 11 KHz. Chemical shifts were referenced via a replacement sample of glycine (carboxyl carbon chemical shift assigned as 176.03 ppm relative to the signal of tetramethylsilane).

EXAMPLES

Eltrombopag starting material can be prepared according to methods known from the literature (for example U.S. Pat. No. 7,160,870)

Example 1 Preparation of Eltrombopag Choline Form A

Eltrombopag free acid (50.0 g) was charged in a round bottom flask and added ethyl acetate (360 mL) and methanol (90 mL) at 20-30° C. The heterogeneous reaction mass was heated up to 50-55° C. Then, added 27.5 g of Choline hydroxide solution (~49.72%) to reaction mass solution under stirring and it turned to very dark wine red colored clear solution then immediately precipitation was observed. Reaction mass was maintained for 1-2 hours at 50-55° C. and gradually cooled to 20-30° C. within 0.5-1 hour and maintained for 1-2 hours under stirring at 24-30° C. Reaction mixture was filtered and washed with a mixture of ethyl acetate & Methanol 80:20 ratio (100 mL) and was kept under suction for 10-15 minutes. Wet cake was dried under vacuum at 20-30° C. for 2 hours and then at 75-80° C. for 16 hours. The obtained solid material (Yield: 55.0 g) was analyzed by XRPD, form A was obtained. PXRD pattern is shown in FIG. 1. Form A is an Eltrombopag Choline (1:1) salt.

Example 2: Preparation of Eltrombopag Choline Form B

Eltrombopag free acid (50.0 g) was charged in a round bottom flask and added ethyl acetate (450 mL) at 20-30° C. The heterogeneous reaction mass was heated up to 50-55° C. Then, added 28.5 g of aqueous Choline hydroxide solution (~48%) to reaction mass solution under stirring. Reaction mass was maintained for 1 hour at 50-55° C. and gradually cooled to 20-30° C. within 0.5-1 hour and maintained for 1-2 hours under stirring at 24-30° C. Reaction mixture was filtered and washed with a mixture of ethyl acetate & methanol (80:20 ratios) 100 mL and was kept under suction for 10-15 minutes. Wet cake was dried under vacuum at 20-30° C. for 2 hours then temperature was raised to 75-80° C. and dried for 22 hours. The obtained solid material (Yield: 58.0 g) was analyzed by XRPD, form B was obtained. PXRD pattern is shown in FIG. 2.

Example 3: Preparation of Eltrombopag Acid THF Solvate

Eltrombopag free acid (156 g) was suspended in THF (1560 mL) at room temperature and heated to reflux in a 3 L reactor. The suspension was stirred under reflux. A solution was formed and stirred under reflux for an additional hour. The solution was cooled to 40° C. in half an hour and filtrated. 1560 mL of water was added drop wise to the filtrate over half an hour and the suspension was stirred for an additional hour at 40° C. The suspension was cooled to 25° C. and stirred for an additional hour. The crystals were filtrated off and washed with 240 mL Methanol:water (1:1). The orange crystals were dried under vacuum at 50° C. until constant weight (168.0 g, yield 94.7%).

Example 4: Preparation of Eltrombopag Choline Form A

Eltrombopag acid (THF solvate, 100 g), ethyl acetate (741 mL) and methanol (82.3 mL) were charged into a 1 L round bottom flask at 20-30° C. The reaction mixture was heated to 50-55° C. and maintained for 10-15 min at same temperature. Then 55.6 g of aqueous choline hydroxide solution (approx. 49.56%) were added under stirring and immediate crystallization was observed. The reaction mass was maintained for 1-2 hr at 50-55° C. and then the reaction mass was cooled to 20-30° C. within 30-60 min and maintained for 1-2 hr at 24-30° C. The obtained solid was filtered under vacuum at 20-30° C. and washed with 274 ml 90:10 ratio of ethyl acetate and methanol mixture for 15-20 minutes. The wet cake was dried under vacuum at 20-30° C. for 2 hr and further dried at 75-80° C. for 8-16 hrs to obtain 112.1 g of Eltrombopag choline Form A.

Example 5: Preparation of Eltrombopag Choline Form B

Methyl ethyl ketone (MEK, 400 ml) and 27.6 g of aqueous choline hydroxide solution (approx. 49.56%) at 20-30° C. were charged into a 1 L round bottom flask under stirring. Then 50 g of eltrombopag free acid was added and the reaction mass was stirred for 6 hrs at 20-30° C. The obtained solid was filtered under vacuum at 20-30° C., washed with 100 ml of MEK and then kept under vacuum suction for 15-20 min at 20-30° C. The wet cake was dried in a vacuum oven at 20-30° C. for 2 hrs and further dried at 75-80° C. under vacuum oven for 10-18 hrs to obtain 56 g of Eltrombopag choline Form B.

Example 6: Preparation of Eltrombopag Choline Form C

Eltrombopag choline (Form A, 50 mg) was taken in a 2 mL vial and 2-Methoxyethanol (1 mL) was added at 25-30° C. The obtained slurry was stirred for 7 days at 60° C. The obtained solid was filtered under vacuum and kept under suction for about 10 minutes at 25° C. to obtain eltrombopag choline Form C.

Example 7: Preparation of Eltrombopag Choline Form C

Eltrombopag choline (Form A; 50 mg) was taken in a 2 ml vial and 2-Methoxyethanol (1 mL) was added at 25-30° C. The obtained slurry was stirred for 24 hrs at 60° C. The obtained solid was filtered under vacuum and kept under suction for about 10 minutes at about 25° C. to obtain eltrombopag choline Form C.

Example 8: Preparation of Amorphous Eltrombopag Choline

Eltrombopag Choline Salt (Form A, 0.2 g) was dissolved in methanol (10 mL) at 45-50° C. to obtain a clear solution. The reaction mixture was subjected to rotoa-buchi distillation under reduced pressure at 45-50° C. Solid material was collected at 22-25° C. The obtained solid was amorphous form of Eltrombopag Choline Salt as analyzed by XRD. (Yield: 0.16 g).

Example 9: Preparation of Amorphous Eltrombopag Choline

Eltrombopag Choline Salt (Form A, 10.0 g) was taken in a flask and dissolved in methanol (1000 mL) under stirring at 30-35° C. for about one hour. The solution was filtered to remove any undissolved particulates. The clear solution was then subjected to spray drying in a laboratory spray dryer (Model: Buchi Mini spray dryer B-290) with feed rate of the solution 4 mL/minute and inlet temperature at 95° C. and outlet temperature of about 66-69° C. with 100% aspiration. After the solution feeding, the system was fed with fresh methanol (about 50 mL) under identical condition and then cooled down to room temperature (22-25° C.). The obtained solid was amorphous form of Eltrombopag Choline Salt analyzed by XRD (Yield: 2.8 G).

The invention claimed is:

1. A solid state form of Eltrombopag choline selected from:
A. crystalline form A, which is characterized by data selected from one or more of the following:
  i. an XRPD pattern having peaks at 11.3, 14.7, 15.4, 16.0 and 24.1 degrees-2-theta±0.2 degrees-2-theta;
  ii. an XRPD pattern as depicted in FIG. 1; and combinations of any i-ii, or
B. crystalline form B, which is characterized by data selected from one or more of the following:
  i. an XRPD pattern having peaks at 7.0, 10.2, 13.9, 14.9, 18.3, 21.6 and 26.0 degrees 2-theta±0.2 degrees 2-theta;
  ii. an XRPD pattern as depicted in FIG. 2; and combinations of any i-ii, or
C. crystalline form C, which is characterized by data selected from one or more of the following:
  i. an XRPD pattern having peaks at 10.9, 14.2, 15.5, 21.9 and 26.9 degrees 2-theta±0.2 degrees 2-theta;
  ii. an XRPD pattern as depicted in FIG. 5; and combinations of any i-ii.

2. The crystalline Form A of eltrombopag choline according to claim 1, which is characterized by data selected from one or more of the following:

i. an XRPD pattern having peaks at 11.3, 14.7, 15.4, 16.0 and 24.1 degrees-2-theta±0.2 degrees-2-theta;

ii. an XRPD pattern as depicted in FIG. 1.

3. The crystalline Form A of eltrombopag choline according to claim 1, which is characterized by an XRPD pattern having peaks at 11.3, 14.7, 15.4, 16.0 and 24.1 degrees 2-theta±0.2 degrees 2-theta, and also having one, two, three, four, five, six or seven additional peaks selected from 12.0, 12.7, 14.1, 20.3, 20.9, 24.8 and 27.0 degrees 2-theta±0.2 degrees 2-theta.

4. The crystalline Form B of eltrombopag choline according to claim 1, which is characterized by data selected from one or more of the following:

i. an XRPD pattern having peaks at 7.0, 10.2, 13.9, 14.9, 18.3, 21.6 and 26.0 degrees 2-theta±0.2 degrees 2-theta;

ii. an XRPD pattern as depicted in FIG. 2.

5. The crystalline Form B of eltrombopag choline according to claim 1, which is characterized an XRPD pattern having peaks at 7.0, 10.2, 13.9, 14.9, 18.3, 21.6 and 26.0 degrees 2-theta±0.2 degrees 2-theta, and also having one, two, three, or four additional peaks selected from 7.4, 16.7, 19.9 and 23.9 degrees 2-theta±0.2 degrees 2-theta.

6. The crystalline Form C of eltrombopag choline according to claim 1, which is characterized by data selected from one or more of the following:

i. an XRPD pattern having peaks at 10.9, 14.2, 15.5, 21.9 and 26.9 degrees 2-theta±0.2 degrees 2-theta;

ii. an XRPD pattern as depicted in FIG. 5.

7. The crystalline Form C of eltrombopag choline according to claim 1, which is characterized by an XRPD pattern having peaks at 10.9, 14.2, 15.5, 21.9 and 26.9 degrees 2-theta±0.2 degrees 2-theta, and also having one, two, three, or four additional peaks selected from 11.3, 15.0, 21.2, 22.5 and 25.6 degrees 2-theta±0.2 degrees 2-theta.

8. A pharmaceutical composition comprising the crystalline form according to claim 1.

9. Use of the crystalline form according to claim 1 in the preparation of pharmaceutical compositions and/or formulations.

10. A pharmaceutical formulation comprising the crystalline form according to claim 1, and at least one pharmaceutically acceptable excipient.

11. The crystalline form according to claim 1, for use as a medicament.

12. The crystalline form according to claim 1, for use in the treatment of Idiopathic thrombocytopenic purpura, Thrombocytopenia and Aplastic anemia.

13. A method of treating Idiopathic thrombocytopenic purpura, Thrombocytopenia and Aplastic anemia comprising administering a therapeutically effective amount of the crystalline form according to claim 1 to a subject suffering from said condition, or otherwise in need of the treatment.

* * * * *